United States Patent [19]

Mitscher

[11] 4,405,522
[45] Sep. 20, 1983

[54] ANTHRACYCLINE SYNTHESIS

[75] Inventor: Lester A. Mitscher, Lawrence, Kans.

[73] Assignee: Adria Laboratories Inc., Columbus, Ohio

[21] Appl. No.: 340,434

[22] Filed: Jan. 18, 1982

[51] Int. Cl.$^3$ .................... C07C 50/34; C07C 50/16
[52] U.S. Cl. ................................ 260/365; 260/383; 260/384
[58] Field of Search .................. 260/351.5–351.1, 260/365, 376–383, 384

[56] References Cited

U.S. PATENT DOCUMENTS

| | | | |
|---|---|---|---|
| 3,019,260 | 1/1962 | McCormick et al. | 260/351.5 |
| 3,201,424 | 8/1965 | McCormick et al. | 260/351.5 |
| 4,021,457 | 5/1977 | Kende et al. | 260/383 |
| 4,215,062 | 7/1980 | Mitscher | 260/365 |

OTHER PUBLICATIONS

Krohn et al., "Regio- und stereoselektive Synthese der α-, β- und γ-Rhodomycinone über intramolekulare Marschalk-Cyclisierung", *Chem. Ber.*, vol. 113, pp. 2994–3009, (1980).

Krohn et al., "Stereoselective Total Synthesis of Anthracyclinones", *Chem. Ber.*, vol. 111(12), pp. 3823–3837, 1978.

Kende et al., "A Regiospecific Total Synthesis of (±)-Daunomycinone", *Tetrahedron Letters*, No. 14, pp. 1201–1204, 1979.

Kende et al., "Total Synthesis of (±)-Daunomycinone and (±)-Carminomycinone", *Journal of American Chemical Society*, vol. 98, No. 7, pp. 1967–1969, 1976.

*Primary Examiner*—Natalie Trousof
*Assistant Examiner*—Raymond K. Covington
*Attorney, Agent, or Firm*—Marion C. Staves

[57] ABSTRACT

A synthesis of 5,12-dihydroxy-1,3,4-trihydro-2,6,11-tetracenetrione and its derivatives from leucoquinizarin or a derivative of leucoquinizarin. The tetracenetriones are well-known intermediates in the synthesis of compounds related to doxorubicin.

4 Claims, No Drawings

ANTHRACYCLINE SYNTHESIS

The present invention relates generally to a technique for synthesizing doxorubicin and related analogues such as 4-demethoxydaunomycin. More particularly, the present invention relates to a new and improved process for the production of 5,12-dihydroxy-1,3,4-trihydro-2,6,11-tetracenetrione, which is a well-known intermediate in the synthesis of compounds related to doxorubicin. The present invention also pertains to intermediates useful in the synthesis process.

BACKGROUND OF THE INVENTION

Doxorubicin is a known anthracycline antibiotic described in U.S. Pat. No. 3,590,028. Doxorubicin is an antineoplastic agent of established clinical utility. Doxorubicin hydrochloride, available from Adria Laboratories, Inc., under the trademark Adriamycin ®, has been approved by the Food and Drug Administration for use in clinical research, and is one of the most powerful anticancer drugs available against numerous forms of cancer. The analogue, 4-demethoxydaunomycin is a known anthracycline antiobiotic which has been demonstrated to have antitumor activity, as reported in the article by Arcamone et al., Cancer Treatment Reports, Vol. 60, (7) pp. 829-834 (1976).

At present, doxorubicin is produced commercially from a soil fungus by a fermentation process. A suitable fermentation technique for preparing doxorubicin is described in U.S. Pat. No. 3,590,028. Such techniques are inherently expensive and limit the types of molecules that can be produced. Because of the inherent disadvantages of presently available commercial techniques for producing doxorubicin and related compounds, substantial effort has been devoted to developing processes for producing such compounds by chemical synthesis.

Techniques for the synthesis of anthracycline antibiotics such as doxorubicin are known. See, e.g., U.S. Pat. No. 4,244,880 to Alexander et al.; Krohn et al., Chem. Ber. 111, pp. 3823-3837 (1978); Krohn et al., Liebigs Ann. Chem., pp. 2011-2017, (1979); U.S. Pat. No. 4,021,457 to Kende et al.; and Kende et al., Journal of the Americal Chemical Society, Vol. 98, No. 7, pp. 1967-1969 (1976). None of the known techniques for the total synthesis of anthracycline antibiotics such as doxorubicin have yet been proven to be commercially successful. Because of the demand for, and scarcity of these compounds, a suitable synthesis technique is highly desired.

The present invention provides a practical technique for synthesizing compounds related to doxorubicin from readily available and inexpensive starting materials. Specifically, and in accordance with the present invention, doxorubicin related compounds may be synthesized from leucoquinizarin. In addition, the present invention provides valuable intermediate compounds that are useful in synthesizing compounds related to doxorubicin.

SUMMARY OF THE INVENTION

Anthracycline antitumor antibiotics such as doxorubicin, daunomycin, 4-demethoxydaunomycin and carminomycin, including their aglycones, are conventionally prepared from intermediate tetracenetrione ketones such as 5,12-dihydroxy-1,3,4-trihydro-2,6,11-tetracenetrione, according to well-known techniques more specifically described below.

In accordance with the present invention and as more fully described below, the tetracenetrione ketone is synthesized starting from leucoquinizarin, a well-known and inexpensive compound or a derivative of leucoquinizarin. A 3-propionate side chain is first added to the leucoquinizarin by a "Marschalk-type" reaction. The resulting quinone monoester is then reduced by catalytic hydrogenation to a second leuco base and a second "Marschalk-type" reaction is conducted with a glyoxylic acid ester. A ring is then formed by base-catalyzed cyclization of the diesters. Finally, the remaining ester group is removed to obtain the 5,12-dihydroxy-1,3,4-trihydro-2,6,11-tetracenetrione. The steps of the synthesis can be shown as follows:

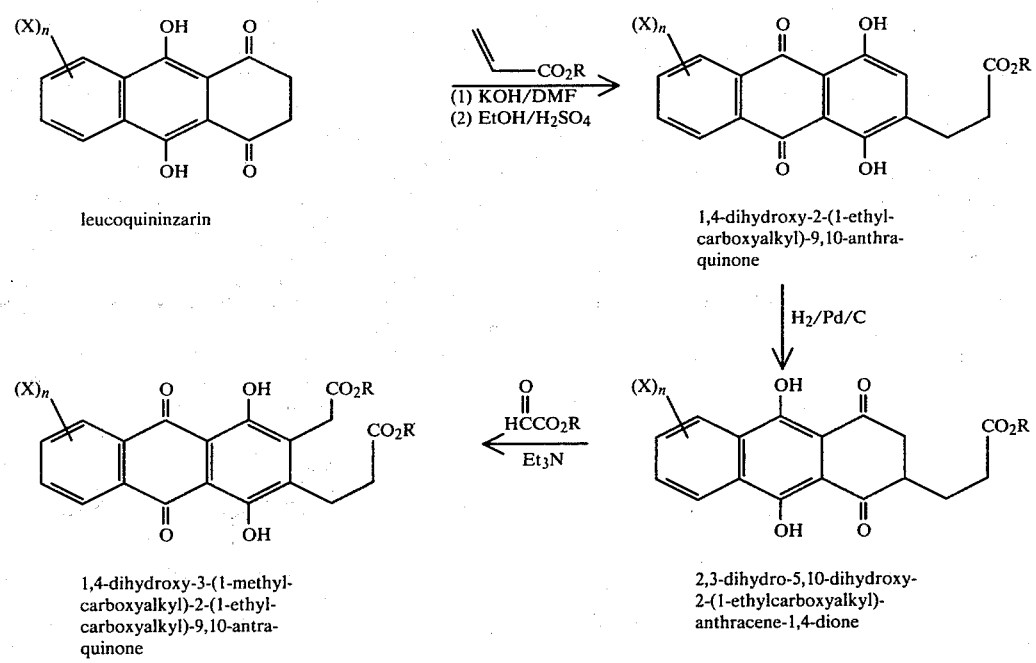

leucoquininzarin 1,4-dihydroxy-2-(1-ethyl-carboxyalkyl)-9,10-anthraquinone 2,3-dihydro-5,10-dihydroxy-2-(1-ethylcarboxyalkyl)-anthracene-1,4-dione 1,4-dihydroxy-3-(1-methyl-carboxyalkyl)-2-(1-ethyl-carboxyalkyl)-9,10-antraquinone

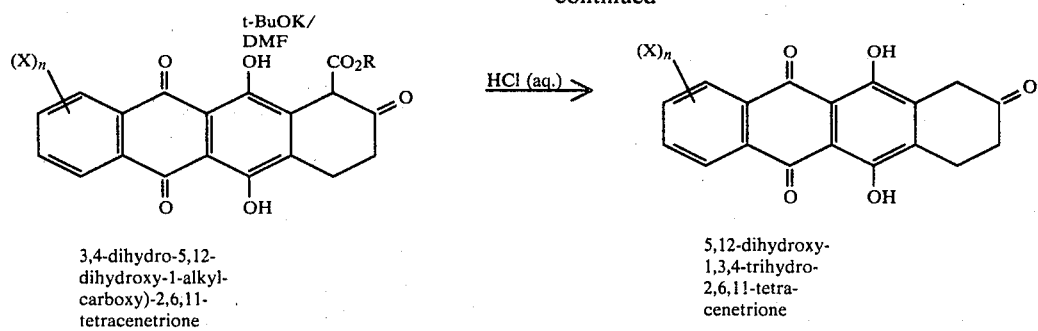

3,4-dihydro-5,12-
dihydroxy-1-alkyl-
carboxy)-2,6,11-
tetracenetrione

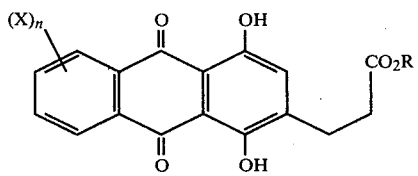

5,12-dihydroxy-
1,3,4-trihydro-
2,6,11-tetra-
cenetrione

In the above synthesis, X is —OH, —CH$_3$, —OCH$_3$ or Cl; n is an integer from 0–2, where n is 2 the X's will be symmetrically substituted on the ring and R is a C$_1$–C$_3$ alkyl. It should be noted that it is very important to introduce the 3-propionate side chain prior to the 2-acetate. If one tries to conduct the synthesis by first reacting the leucoquinizarin with a glyoxylate, the yield will be drastically reduced and side reactions increased.

The present invention also provides valuable intermediates useful in the synthesis, including those having the formulas:

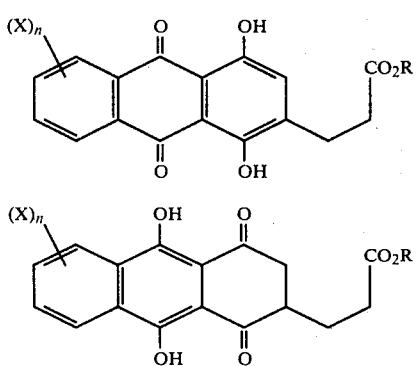

where X, n and R are as defined above.

DESCRIPTION OF PREFERRED EMBODIMENTS

In the synthesis of the present invention, readily available and inexpensive leucoquinizarin or a derivative of leucoquinizarin is utilized in double sequential "Marschalk-type" reactions, followed by a "Dieckmann-type" condensation. In the first step of the synthesis, a 3-propionate side chain is introduced by reacting an acrylate, such as ethyl acrylate, with the leucoquinizarin in a mixture of potassium hydroxide and dimethyl formamide. The crude reaction product, containing both the ester and its hydrolyzed analogue, is boiled in ethanol with a few drops of concentrated sulfuric acid prior to purification to re-esterify the hydrolyzed product. The product has the following formula:

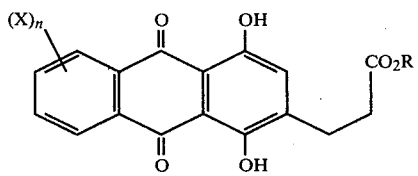

(1)

Although quinizarin can easily be reduced to leucoquinizarin by sodium dithionite in aqueous sodium hydroxide, the above quinone monoester cannot be reduced in good yield by this procedure. Therefore, the reduction of compound (1) to its leuco analogue is accomplished by catalytic hydrogenation using palladium/carbon catalyst in ethanol/tetrahydrofuran. The leuco product has the following formula:

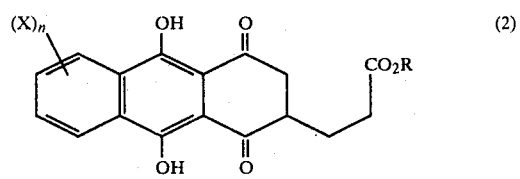

(2)

The leucomonoester (2) is treated with a glyoxylate, such as ethyl glyoxylate, the triethylamine in deoxygenated ethanol at reflux to obtain the diester compound having the following formula:

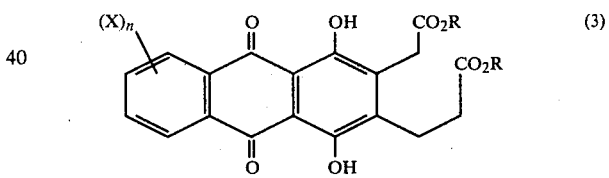

(3)

It is important that the above reaction be conducted at reflux, since the reaction conducted at room temperature yields an undesired diester.

The above diester compound (3) is subjected to a "Dieckmann-type" condensation by treating the diester with potassium t-butoxide in dimethylformamide for a short time. The reaction time is very important, since the presence of a ketone functionality in the D-ring makes it susceptible to aromatization. In accordance with the instant invention, it has been found that about three minutes, i.e., two and one half to three and one half minutes, is the optimum time for the reaction under the conditions and reactants chosen. The product has the following formula:

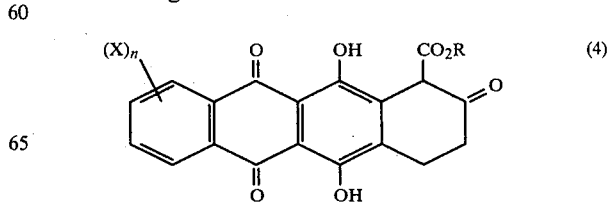

(4)

The above compound (4) is treated with a 9 molar hydrochloric acid aqueous solution in ethanol, at reflux for about 24 hours to obtain the ketone product having the following formula:

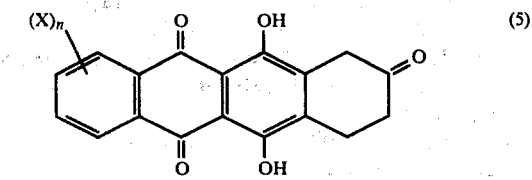

The above ketones (5) are established intermediates in the total synthesis of anthracycline antitumor antibiotics such as daunomycin, 7-demethoxydaunomycin, etc. (See A. S. Kende et al., J. Amer. Chem. Soc., 98, p. 1967 (1976).

The following examples further illustrate preferred embodiments of the present invention. The examples should in no way be considered limiting, but are merely illustrative of the various features of the present invention.

EXAMPLE 1

Finely ground potassium hydroxide (0.069 mmole) is suspended in 20 milliliters of dry dimethylformamide in a 225 ml. three-neck round bottom flask fitted with a magnetic stirring bar, two dropping funnels, and a rubber septum with an inlet and outlet. A solution of 0.033 mole of leucoquinizarin in 80 ml. of dry dimethylformamide is placed in one of the dropping funnels and 0.040 mole of ethyl acrylate is placed in the other dropping funnel. The entire system is flushed with nitrogen for about 10 minutes, then placed under an atmosphere of nitrogen. The leucoquinizarin solution is added to the potasssium hydroxide dimethylformamide suspension, followed immediately by the ethyl acrylate. The reaction mixture is vigorously stirred at 65° C. in a preheated oil bath for 75 minutes under nitrogen. The heat is removed and the nitrogen flow is replaced with a dry air flow bubbling in the reaction mixture for 5 minutes. The reaction is then quenched with glacial acetic acid with cooling in an ice-water bath. The reaction mixture is poured into 300 ml. of water, the suspension made slightly acid with 10% aqueous hydrochloric acid and stirred vigorously with a glass rod. The orange gummy product is collected by filtration, dissolved in ethylacetate, washed with water, dried over sodium sulfate and concentrated at a reduced pressure to yield an orange crystalline product containing both the ester and its hydrolyzed carboxylic acid derivative. This crude material is then suspended in 100 ml. of 95% ethanol and 5 drops of concentrated sulfuric acid added. The suspension is stirred at reflux for 11½ hours. The solvent is distilled off at reduced pressure to about 20 ml., the residue diluted with water and then extracted with ethylacetate. The extract is washed with water, dried over sodium sulfate, then concentrated at reduced pressure to yield a solid brownish product. Chromatography on a silica gel column (90 g. of silica gel) in benzene/ethyl acetate/ethyl alcohol (100:5:2) affords an 85% yield of the monoester having the formula:

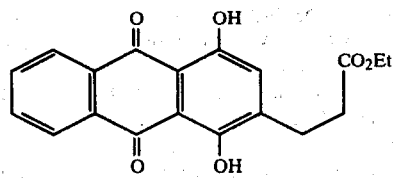

The orange crystalline product has a melting point of 116°–118° C. Analysis calculated for $C_{19}H_{16}O_6$: C, 67.06, H, 4.74; found: C, 67.16, H, 4.80. NMR (CDCl$_3$) δ 1.30 (3H, t, J=7 Hz, CH$_2$CH$_3$), 2.85 (4H, m, ArCH$_2$CH$_2$CO$_2$), 4.19 (2H, q, J=7 Hz, OCH$_2$CH$_3$), 7.10 (1H, s, C$_3$ArH), 8.00 (4H, sym. m, ArH), 12.37 (1H, s, ArOH) and 12.85 (1H, s, ArOH). Infrared spectrum (nujol) 1727 cm$^{-1}$ (CO$_2$CH$_2$CH$_3$), 1625 (C=O), 1590, 1475, 1430, 1410, 1345, 1300, 1280, 1245, 1195, 1160, 1120, 1050, 1020, 970, 955, 920, 800, 775 and 740.

EXAMPLE 2

Into a 250 ml. hydrogenation flask containing a sidearm inlet is placed 0.25 g. of palladium/carbon catalyst and 50 ml. ethanol. The catalyst was prehydrogenated until no further uptake was observed. A sample of the product from Example 1 (7.34 mmoles) is dissolved in 50 ml. of tetrahydrofuran and added through the sidearm inlet to the ethanol suspension of catalyst. The dark red-brown suspension, which forms, is stirred vigorously and hydrogenated overnight at room temperature. An intense green-yellow suspension is obtained. The hydrogen uptake, after correction for room temperature difference from S.T.P., is 185 ml. (113% of theory). The suspension is filtered and the filtrate evaporated at 40°–50° C. under reduced pressure. The resulting orange solid is recrystallized from methanol to yield 77% of theory of the leuco monoester having the formula:

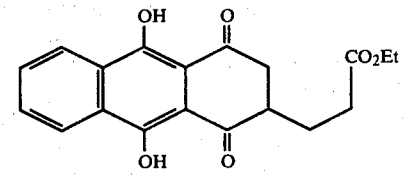

The light orange crystalline product has a melting point of 115.5°–117° C. Analysis calculated for $C_{19}H_{18}O_6$: C, 66.66; H, 5.30; found C, 66.48; H, 5.31. NMR (CDCl$_3$ δ 1.12 (3H, t, J=8 Hz, CH$_2$CH$_3$), 2.00–2.50 (4H, m, CH$_2$CH$_2$CO$_2$), 3.00 (3H, broad t, CH and CH$_2$CO), 4.13 (2H, q, J=8 Hz, OCH$_2$CH$_3$), 8.10 (4H, sym. m, ArH) and 13.48 (2H, d, ArOH). Infrared spectrum (KBr) 3000 cm$^{-1}$, 1732 (CO$_2$CH$_2$CH$_3$), 1634 (C=O), 1612, 1580, 1502, 1470, 1390, 1370, 1300, 1280, 1260, 1245, 1180, 1090, 1050, 1030, 820 and 770.

EXAMPLE 3

Into a 250 ml. pre-dried, three-neck reaction flask containing a magnetic stirring bar is placed 4.09 mmoles of the leuco monoester product of Example 2 and 7.25 mmoles of ethyl glyoxylate. The flask is fitted with a condenser and a septum adapter and connected to a condenser from a still containing deoxygenated ethanol. The apparatus is flushed with nitrogen, and about 30 ml. of deoxygenated ethanol is distilled into the reaction flask. The flask is disconnected from the ethanol still and 24.5 mmoles of triethylamine is added dropwise to the flask via a syringe. The resulting brownish suspension is stirred at room temperature for 2 hours and 20 minutes, then heated at reflux (~115° C.) for 5¾ hours. On cooling, the dark reaction mixture becomes a crystalline mass. The mixture is poured into ice-water (150 ml.) containing acetic acid (1.5 ml.) and stirred for one hour. The mixture is then filtered and the collected solid washed with water. The solid is dried at about 30° C. under vacuum for 10 hours. The residue (90% of theory) is crystallized from 50 ml. of ethanol and the solution allowed to cool in the refrigerator overnight. Upon filtration and drying at 50° C. under vacuum, there is obtained the diester having the formula:

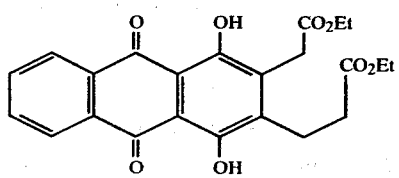

The orange crystalline product has a melting point of 155°–156.5° C. (after recrystallization from ethanol). Analysis calculated for $C_{23}H_{22}O_8$: C, 64.78; H, 5.20; found C, 65.00; H, 5.30. NMR (CDCl$_3$) δ 1.27 (6H, t, CH$_2$CH$_3$), 2.72 (4H, sym. m, ArCH$_2$CH$_2$CO$_2$), 3.95 (2H, s, ArCH$_2$CO$_2$), 4.17 (4H, q, OCH$_2$CH$_3$), 8.09 (4H, sym. m, ArH) and 11.41 (2H, s, ArOH). Infrared spectrum (KBr) 2982 cm$^{-1}$, 1739 (CO$_2$CH$_2$CH$_3$), 1628 (C=O), 1586, 1450, 1420, 1390, 1370, 1330, 1305, 1270, 1200, 1170, 1120, 1040, 1020, 990, 950, 800, 770 and 725.

EXAMPLE 4

Into a predried 100 ml. reaction flask containing a magnetic stirring bar is placed 0.645 mmole of the diester product of Example 3 and 10 ml. of dimethylformamide. The flask is fitted with a septum adapter and flushed with nitrogen. The stirred mixture is warmed slightly to effect solution, then allowed to cool to room temperature. Solid potassium t-butoxide (2.03 mmoles) is added to the flask and the mixture stirred vigorously for exactly three minutes. The intense blue suspension is cooled in an ice bath for 30 seconds and then acidified by the dropwise addition of glacial acetic acid (0.25 ml.). The dark greenish mixture is stirred at room temperature for 1 minute and then poured into 50 ml. of brine. A red suspension is formed, shaken vigorously and filtered. The filtered solid is partitioned between ethylacetate (100 ml.) and water. After separation, the ethylacetate phase is washed twice with water and then four times with 10% aqueous sodium carbonate. Finally, the ethylacetate phase is washed with brine containing 3 drops of acetic acid, dried over magnesium sulfate, filtered and evaporated under reduced pressure. The dark red-brown solid is crystallized from tetrahydrofuran/ether to yield (40% of theory) the compound having the formula:

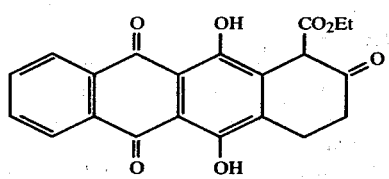

The glisteneing brown crystalline product has a melting point of 164°–166° C. NMR (DOAc-d$_4$) δ 1.26 (3H, t, J=8 Hz, CH$_2$CH$_3$), 3.04 (4H, m, ArCH$_2$CH$_2$CO), 4.22 (2H, q, J=8 Hz, CH$_2$CH$_3$) and 8.12 (4H, sym. m, ArH). Infrared spectrum (KBr) 2978 cm$^{-1}$, 1740 (CO$_2$Et), 1723 (C=O), 1623 (C=O), 1587, 1440, 1420, 1405, 1370, 1335, 1300, 1270, 1225, 1175, 1150, 1120, 1090, 1060, 1015, 810, 780 and 720. Mass spectrum m/e 380 M$^+$), 334 (83%) (M—CH$_3$CH$_2$OH), 307 (100%) (M—CO$_2$CH$_2$CH$_3$), 306 (M—CH$_3$CH$_2$OH—CO), 289 (M—CO$_2$CH$_2$CH$_3$—H$_2$O), 288 (M—CH$_3$CH$_2$OH—CO—H$_2$O).

EXAMPLE 5

Into a 10 ml. single neck reaction flask containing a magnetic stirring bar is placed 0.052 mmole of the product of Example 4, 2 ml. absolute ethanol and 4 ml. of 9 M hydrochloric acid. The flask is fitted with a condenser, filled with nitrogen and placed in a preheated oil bath (~120° C.). The red suspension is held at reflux for 25 hours, then cooled in an ice-water bath and filtered. The red solid is washed well with water and dried at 56° C. under vacuum overnight. The solid is dissolved in 12 ml. of tetrahydrofuran, filtered through a pad of celite and then boiled at atmospheric pressure to reduce the volume about half. A crystalline precipitate develops rapidly when the solution reaches room temperature. After refrigeration overnight, the precipitate is filtered and dried to yield 55% of the theoretical quantity of a red-brown crystalline solid having the formula:

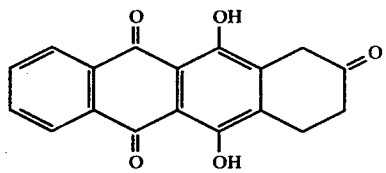

The above product co-chromatographed with an authentic sample of 5,12-dihydroxy-1,3,4-trihydro-2,6,11-tetracenetrione. Analysis calculated for $C_{18}H_{12}O_5$: C, 70.13; H, 3.92; found C, 70.28; H, 3.99. NMR (CDCl$_3$) 2.67 (2H, t, ArCH$_2$CH$_2$CO), 3.28 (2H, t, ArCH$_2$CH$_2$CO), 3.67 (2H, s, ArCH$_2$O), 8.10 (4H, sym. m, ArH), 13.35 (1H, s, ArOH) and 13.45 (1H, s, ArOH). Infrared spectrum (KBr) 1727 cm$^{-1}$ (C=O), 1622 (C=O), 1581, 1450, 1425, 1400, 1370, 1340, 1315, 1295, 1280, 1260, 1250, 1230, 1200, 1120, 995, 960, 820, 790 and 720.

What I claim and desire to protect by Letters Patent is:

1. A process for producing a 5,12-dihydroxy-1,3,4-trihydro-2,6,11-tetracenetrione compound having the formula:

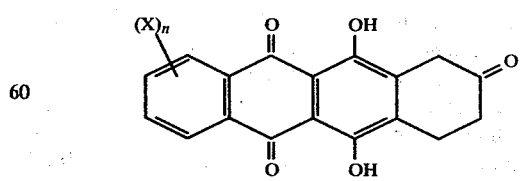

where X is selected from —OH, —CH$_3$, —OCH$_3$, and Cl and n is an integer from 0–2 and when n is 2 the X's are symmetrically substituted on the ring; said process comprising:

(a) reacting a $C_1$-$C_3$ alkyl acrylate with a leucoquinizarin having the formula:

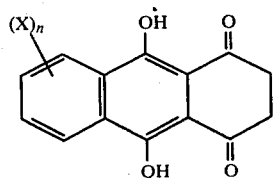

where X and n are as defined above, to produce 1,4-dihydroxy-2-(1-ethylcarboxy alkyl)-9,10-anthraquinone;

(b) reducing the compound of (a) by catalytic hydrogenation to produce 2,3-dihydro-5,10-dihydroxy-2-(1-ethylcarboxy alkyl)-anthracene-1,4-dione;

(c) reacting the compound of (b) with a $C_1$-$C_3$ alkyl glyoxylate to produce 1,4-dihydroxy-3-(1-methylcarboxy alkyl)-2-(1-ethylcarboxy alkyl)-9,10-anthraquinone;

(d) cyclization of the compound of (c) to produce 3,4-dihydro-5,12-dihydroxy-1-(alkyl-carboxy)-2,6,11-tetracenetrione; and (e) decarboxylation of the compound of (d) to produce the 5,12-dihydroxy-1,3,4-trihydro-2,6,11-tetracenetrione compound whose formula is shown above.

2. The process of claim 1 where n is 0.

3. A process for producing 1,4-dihydroxy-3-(1-methylcarboxy ethyl)-2-(1-ethylcarboxy ethyl)-9,10-anthraquinone comprising:

a. reacting ethyl acrylate with leucoquinizarin to produce 1,4-dihydroxy-2-(1-ethylcarboxy ethyl)-9,10-anthraquinone;

b. reducing the compound of (a) by catalytic hydrogenation to produce 1,2-dihydro-5,10-dihydroxy-2-(1-ethylcarboxy ethyl)-anthracene-1,4-dione; and c. reacting the compound of (b) with ethyl glyoxylate to produce 1,4-dihydroxy-3-(1-methylcarboxy ethyl)-2-(1-ethylcarboxy ethyl)-9,10-anthraquinone.

4. A compound having the formula:

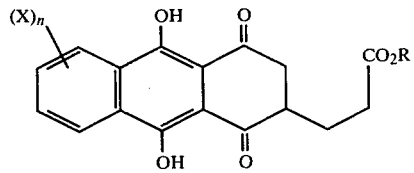

where X is selected from —OH, —$CH_3$, —$OCH_3$ and —Cl; n is an integer from 0-2 and when n is 2 the X's are symmetrically substituted on the ring; and R is a $C_1$-$C_3$ alkyl.

* * * * *

UNITED STATES PATENT AND TRADEMARK OFFICE
CERTIFICATE OF CORRECTION

PATENT NO. : 4,405,522
DATED : September 20, 1983
INVENTOR(S) : Lester A. MITSCHER It is certified that error appears in the above–identified patent and that said Letters Patent are hereby corrected as shown below:

On the cover sheet of the patent the Assignee reads

"Adria Laboratories Inc., Columbus, Ohio" and should read

-- The University of Kansas
   Center for Research, Incorporated,
   Lawrence, Kansas -- .

Signed and Sealed this

Sixth Day of December 1983

[SEAL]

Attest:

GERALD J. MOSSINGHOFF

Attesting Officer

Commissioner of Patents and Trademarks